United States Patent [19]

Yokota et al.

[11] Patent Number: 5,191,096

[45] Date of Patent: Mar. 2, 1993

[54] PROCESS FOR PRODUCING OMEGA-HYDROXY FATTY ACIDS

[75] Inventors: Tadafumi Yokota; Akio Watanabe, both of Toda, Japan

[73] Assignee: Nippon Mining Co., Ltd., Japan

[21] Appl. No.: 826,638

[22] Filed: Jan. 23, 1992

Related U.S. Application Data

[63] Continuation of Ser. No. 319,155, Mar. 6, 1989, abandoned.

[30] Foreign Application Priority Data

Dec. 7, 1987 [JP] Japan .................................. 62-307417
Jul. 18, 1988 [JP] Japan .................................. 63-177222
Aug. 3, 1988 [JP] Japan .................................. 63-192692

[51] Int. Cl.$^5$ ...................... C07C 51/10; C07C 51/15; C07C 59/00
[52] U.S. Cl. .................................. 554/129; 554/132; 554/154; 562/579
[58] Field of Search ............. 562/579; 260/413; 554/129, 132, 154

[56] References Cited

U.S. PATENT DOCUMENTS 3,708,534 1/1973 Oshimoto ........................ 260/413
3,781,350 12/1973 Fujita et al. ..................... 260/413

FOREIGN PATENT DOCUMENTS 0262948 4/1988 European Pat. Off. ............ 260/413

*Primary Examiner*—José G. Dees
*Assistant Examiner*—Joseph M. Conrad, III
*Attorney, Agent, or Firm*—Parkhurst, Wendel & Rossi

[57] ABSTRACT

ω-Hydroxy fatty acids usable for the synthesis of medicaments, perfumes and polymers are produced by subjecting an alkali or alkaline earth metal salt of long-chain dicarboxylic acid monoester to a reduction with a borohydride compound or catalytic hydrogenating reduction treatment.

5 Claims, No Drawings

PROCESS FOR PRODUCING OMEGA-HYDROXY FATTY ACIDS

This is a Continuation of application Ser. No. 07/319,155 filed Mar. 6, 1989, now abandoned.

BACKGROUND OF THE INVENTION

1. Field of the Invention

This invention relates to a process for producing ω-hydroxy fatty acids. ω-Hydroxy fatty acids are useful as a raw material for synthesis of medicaments and perfumes and further are widely used as a raw material for synthesis of various polymers.

2. Related Art Statement

As a process for producing ω-hydroxy fatty acids, there have hitherto been proposed a process for ring-opening ω-hydroxyalkyl-γ-butylolactone or ω-acyloxyalkyl-γ-butylolactone (Japanese Patent Application Publication No. 61-3776), a process of converting 13-oxabicyclo [10,4,0]-hexadecene [1(12)] into a lactone and then ring-opening the lactone (Japanese Patent Application Publication No. 61-21474), and the like.

However, these processes consist of complicated and multi-stage production steps, so that the yield of the final product is low. Further, expensive raw materials are used, so that the production cost is unfavorably increased.

Moreover, there has been known a process of subjecting an ester compound or a carboxylic acid compound to a catalytic hydrogenating reduction [A. Guyer et al., *Helvetica Chimica Acta*, vol. 38, pp976~982(1955)]. However, it is not reported that a compound having an ester group and a carboxyl group in the same molecule is treated by the same manner as mentioned above to selectively reduce only the ester group. In this connection, the inventors have proposed a process in which an inexpensive dicarboxylic acid is used as a raw material and diesterified, half-hydrolyzed into a monoester and then subjected to a hydrogenating reduction in the presence of a copper-chromium oxide catalyst to form ω-hydroxy fatty acid (EP-A-0 262 948).

SUMMARY OF THE INVENTION

The inventors have made further studies for more simplifying the above process and found that the ester group is preferentially reduced when directly using an alkali metal or alkaline earth metal salt of long-chain dicarboxylic acid monoester.

The invention is based on the above knowledge and is to provide a process for cheaply and efficiently producing ω-hydroxy fatty acids at relatively simple steps by using an inexpensive raw material.

According to the invention, there is the provision of a process for producing ω-hydroxy fatty acids, which comprises subjecting an alkali metal or alkaline earth metal salt of a long-chain dicarboxylic acid monoester to a reduction with a borohydride compound or a hydrogenating reduction in the presence of a catalyst.

DESCRIPTION OF THE PREFERRED EMBODIMENTS

As the long-chain dicarboxylic acid monoester, it is preferable to use a monoester of aliphatic dicarboxylic acid having a carbon number of 9~18 for obtaining lactones usable for the synthesis of medicaments or perfumes. According to the invention, the carbon number is not restricted to the above range. The aliphatic dicarboxylic acid includes, 1,9-nonanedioic acid, 1,10-decanedioic acid, 1,11-undecanedioic acid, 1,12-dodecanedioic acid, 1,13-anedioic acid, 1,16-hexadecanedioic acid, 1,17-heptadecanedioic acid, 1,18-octadecanedioic acid, 2-methyl or 3-methyl substituted compounds of these acids, and unsaturated aliphatic dicarboxylic acids such as 9-octadecene-1,18-dioic acid and the like.

The alkali metal or alkaline earth metal salt of such a monoester is obtained by diesterifying the aliphatic dicarboxylic acid with an alcohol or the like, adding a hydroxide of an alkali metal or an alkaline earth metal to convert the diester into a monoester salt as a solid precipitating from the reaction system, and then subjecting to a solid-liquid separation [*Organic Synthesis*, Collective Volume 4, pp635~638 (1963)]. As the alkali metal or alkaline earth metal, mention may be made of lithium, sodium, potassium, rubidium, beryllium, magnesium, calcium, strontium, barium and the like. Among them, barium is preferable because the yield of monoester salt can be increased.

As the alcohol for the diesterification, the use of a lower alcohol having a carbon number of 1~4 such as methyl alcohol, ethyl alcohol, propyl alcohol, butyl alcohol or the like is preferable because such an alcohol can easily conduct the separation and purification of the ester product. The diesterification can be carried out by using 1~4 parts by weight of the alcohol per 1 part by weight of the dicarboxylic acid, adding 0~3 parts by weight of an organic solvent such as benzene, toluene, xylene or the like and 0.1~0.5 part by weight of an acid such as sulfuric acid, hydrochloric acid or the like and then heating at a temperature of 60°~120° C. for 0.5~8 hours.

Moreover, the aliphatic dicarboxylic acid is produced at relatively low production cost by oxidizing an alkane having a corresponding carbon number in the presence of a microorganism (U.S. Pat. No. 3,843,466 and 4,275,158).

When a borohydride compound is acted as a reducing agent to the above alkali metal or alkaline earth metal salt of long-chain dicarboxylic acid monoester, it is economically preferable that the amount of the reducing agent used is about 0.5~1 mol based on 1 mol of the dicarboxylic acid monoester residue in the salt. As the borohydride compound, use may be made of lithium borohydride, calcium borohydride, zinc borohydride, magnesium borohydride, potassium borohydride, beryllium borohydride, barium borohydride and the like. Among them, the lithium, calcium borohydride, magnesium borohydride and zinc borohydride are preferable because the reduction can be carried out at a high selectivity. Furthermore, the borohydride compound may be used by mixing with another compound. For example, when the sodium borohydride is used as a mixture with aluminum chloride, the rate of reduction reaction becomes faster. Moreover, the above borohydride compound is obtained by a reaction of lithium borohydride with a corresponding halide, e.g. the lithium borohydride is obtained by the reaction of sodium borohydride with lithium chloride. In this case, there is caused a difference in the activity and selectivity in accordance with not only the kind of the borohydride compound but also the method of preparing the borohydride compound. Particularly, the zinc borohydride obtained by the reaction of sodium borohydride and zinc iodide has very high selectivity and reactivity and is preferable. Moreover, these borohydride compounds are previously prepared and may be added in the reduction reaction, but they may be directly prepared and used in a reaction vessel for the reduction reaction.

The reduction reaction can be carried out by suspending the above borohydride compound in an organic solvent such as diethyleneglycol dimethyl ether, diethyl ether, tetrahydrofuran, dioxane, N,N-dimethyl formamide, dimethylsulfoxide or the like at a concentration of 1~10% by weight, adding dropwise a suspension of the above monoester salt in the same solvent thereto, and stirring them at a temperature of 0°~140° C. for 1~30 hours. Alternately, such a reaction may be carried out by dropwise adding a suspension of the borohydride compound to a suspension of the monoester salt or a suspension of the monoester salt containing a metal halide.

After the completion of the reaction, the resulting reaction product is added to an aqueous solution of an acid such as hydrochloric acid, sulfuric acid, nitric acid, acetic acid or the like to dissipate the unreacted borohydride compound and acidified in order to hydrolyze a barium salt of $\omega$-hydroxy fatty acid, and then filtered to recover the precipitated organic substance, whereby w-hydroxy fatty acid can be obtained.

On the other hand, in the process for a hydrogenating reduction, an ordinary hydrogenation catalyst may be used as a catalyst. Particularly, a copper-chromium oxide catalyst is preferable from a viewpoint of the selectivity to the hydrogenating reduction. This copper-chromium oxide catalyst contains copper oxide and chromium oxide as active components and is preferable to be added with barium, manganese, silica or the like as a promoter. Preferably, a catalyst comprising 40~60% by weight of CuO, 35~55% by weight of $Cr_2O_3$ and not more than 10% by weight of the promoter is used. Of course, a carrier-supported catalyst containing the above components supported on a carrier may be used. As the catalyst, it is convenient and preferred to use a commercially available copper chromite ($CuO \cdot CuCr_2O_4$) catalyst which is used for hydrogenating glycerides to produce higher alcohols [Adkins, *Organic Reaction*, Vol. 8, pp1~27 (1954)].

The hydrogenating reduction reaction is preferable to be carried out at a hydrogen pressure of 50~300 kg/cm$^2$ and a temperature of 150°~350° C., wherein any of a suspension bed system, a fluidized bed system and a fixed bed system can properly be employed. In this case, if the hydrogen pressure is less than 50 kg/cm$^2$ or the temperature is lower than 150° C., the rate of reduction reaction is insufficient and the yield unfavorably lowers. A higher reaction temperature or hydrogen pressure is better because the reaction rate increases to improve the yield. However, if the reaction temperature exceeds 350° C., the decomposition of raw material and product occurs to undesirably reduce the yield, while if the hydrogen pressure is more than 300 kg/cm$^2$, a remarkable improvement in the reaction rate can not be expected, and also the hydrogen pressure above 300 kg/cm$^2$ is unfavorable from viewpoints of economical reasons and safety. Further, it is preferable that a mol ratio of hydrogen to aliphatic dicarboxylic acid monoester residue is 10/1~1000/1. Moreover, the aliphatic dicarboxylic acid monoester salt may be provided for the reduction reaction either directly or after being suspended in a solvent such as dioxane, methanol, tetrahydrofuran, diphenylether, toluene, xylene, benzene, hexane, or diethyleneglycol dimethyl ether. Such reaction conditions can properly be selected by considering the kind of long-chain dicarboxylic acid monoester salt as the raw material, the activity of the catalyst used and further the solvent used.

After the completion of the hydrogenating reduction, the salt of the dicarboxylic acid monoester is converted into a salt of $\omega$-hydroxy fatty acid, which can easily be replaced to a free carboxyl group by contacting with an acid. In this case, a mineral acid such as sulfuric acid, hydrochloric acid, nitric acid or the like and an organic acid such as acetic acid or the like may be used as the acid.

For example, when the thus obtained $\omega$-hyroxy fatty acid is used to produce a macrocyclic lactone, it is polymerized by the known method to form a linear polyester, which is then depolymerized upon heating under a reduced pressure in the presence of a depolymerization catalyst (Japanese Patent Application Publication No. 51-25033).

The following examples are given in illustration of the invention and are not intended as limitations thereof.

EXAMPLE 1

A suspension of 0.76 g (20 mmol) of sodium borohydride in 20 ml of diethyleneglycol dimethyl ether was added with 0.85 g (20 mmol) of lithium chloride, which was stirred at room temperature for 30 minutes. To the resulting suspension was added dropwise a suspension of 7.18 g (20 mmol as dicarboxylic acid) of barium salt of pentadecanedioic acid monomethyl ester in 30 ml of diethyleneglycol dimethyl ether and then stirred at a temperature of 80° C. for 22 hours. After the completion of reaction, the reaction mixture was added to 120 ml of water containing 11 ml of concentrated hydrochloric acid and stirred at room temperature for 30 minutes to precipitate $\omega$-hydroxy pentadecanoic acid. This product was filtered to obtain $\omega$-hydroxy pentadecanoic acid. The purity and yield determined by gas chromatography were 84% and 76%, respectively.

EXAMPLE 2

The same procedure as in Example 1 was repeated except that 7.36 g (20 mmol as dicarboxylic acid) of pentadecanedioic acid monoethyl ester was used instead of pentadecanedioic acid monomethyl ester to obtain $\omega$-hydroxy pentadecanoic acid. In this case, the yield was 70%.

EXAMPLE 3

The same procedure as in Example 1 was repeated except that 6.24 g (20 mmol as dicarboxylic acid) of dodecanedioic acid monomethyl ester was used instead of pentadecanedioic acid monomethyl ester to obtain $\omega$-hydroxy dodecanoic acid. The yield was 70%.

EXAMPLE 4

A suspension of 0.76 g (20 mmol) of sodium borohydride in 20 ml of diethyleneglycol dimethyl ether was added with 2.22 g (20 mmol) of calcium chloride, which was then stirred at room temperature for 30 minutes. Next, a suspension of 7.18 g (20 mmol as dicarboxylic acid) of barium salt of pentadecanedioic acid monomethyl ester in 30 ml of diethyleneglycol dimethyl ether was added dropwise thereto and subsequently stirred at a temperature of 80° C. for 9 hours. After the completion of reaction, the same procedure as in Example 1 was repeated to obtain $\omega$-hydroxy pentadecanoic acid at a yield of 76%.

EXAMPLE 5

The same procedure as in Example 4 was repeated except that 1.90 g (20 mmol) of magnesium chloride was used instead of calcium chloride and the stirring was carried out at 100° C. for 6 hours instead of 80° C., 9 hours to obtain ω-hydroxy pentadecanoic acid. The yield was 88%.

EXAMPLE 6

The same procedure as in Example 4 was repeated except that 2.73 g (20 mmol) of zinc chloride was used instead of calcium chloride and the stirring was carried out at 80° C. for 3 hours to obtain ω-hydroxy pentadecanoic acid. The yield was 84%.

EXAMPLE 7

The same procedure as in Example 6 was repeated except that 3.19 g (10 mmol) of zinc iodide was used instead of zinc chloride to obtain ω-hydroxy pentadecanoic acid. The yield was 94%.

EXAMPLE 8

The same procedure as in Example 6 was repeated except that 2.25 g (10 mmol) of zinc bromide was used instead of zinc chloride to obtain ω-hydroxy pentadecanoic acid. The yield was 46%.

EXAMPLE 9

A suspension of 0.76 g (20 mmol) of sodium borohydride in 50 ml of dioxane was added with 5.45 g (40 mmol) of zinc chloride, which was then stirred at room temperature for 30 minutes. Next, a suspension of 7.18 g (20 mmol as dicarboxylic acid) of barium salt of pentadecanedioic acid monomethyl ester in 50 ml of dioxane was added dropwise thereto and subsequently stirred at a temperature of 80° C. for 9 hours. After the completion of reaction, the same procedure as in Example 1 was repeated to obtain ω-hydroxy pentadecanoic acid at a yield of 82%.

EXAMPLE 10

A suspension of 0.76 g (20 mmol) of sodium borohydride in 20 ml of dimethoxy ethane was added with 2.73 g (20 mmol) of zinc chloride, which was then stirred at room temperature for 30 minutes. Next, a suspension of 7.18 g (20 mmol as dicarboxylic acid) of barium salt of pentadecanedioic acid monomethyl ester in 30 ml of dimethoxy ethane was added dropwise thereto and stirred at a temperature of 80° C. for 9 hours. After the completion of reaction, the same procedure as in Example 1 was repeated to obtain ω-hydroxy pentadecanoic acid at a yield of 35%.

EXAMPLE 11

Into an autoclave of 200 ml capacity were charged 7.08 g (10 mmol) of barium salt of pentadecanedioic acid monomethyl ester, 0.35 g of copper-chromium oxide catalyst (CuO 44 wt %, $Cr_2O_3$ 42 wt %, BaO 6.7 wt %, MnO 3.8 wt %; surface area: 40~60 $m^2/g$) and 25 ml of dioxane, and after sealing therein at an initial hydrogen pressure of 120 kg/$cm^2$, the reaction was performed for 2 hours while heating the mixture at a temperature of 254° C. Then, the solvent was distilled off under a reduced pressure from the reaction product, and 50 ml of water was added to the residue and further an aqueous solution of potassium hydroxide (KOH 2.61 g/10 ml of water) was added to perform hydrolysis for 2 hours upon heating. The hydrolyzed product was added with 100 ml of diethyl ether and 5 ml of concentrated hydrochloric acid to extract the product into the ether layer. The ether layer was washed with an aqueous solution of saturated sodium chloride, dehydrated on anhydrous magnesium sulfate, and then the solvent was distilled off to obtain ω-hydroxy pentadecanoic acid.

The yield determined by gas chromatography was 23%.

EXAMPLE 12

In order to avoid excessive reaction, the same procedure as in Example 11 was repeated except that the reaction time was restricted to 1 hour, whereby ω-hydroxy pentadecanoic acid was obtained. The yield was 37%.

EXAMPLE 13

The same procedure as in Example 11 was repeated except that sodium salt (20 mmol) of pentadecanedioic acid monomethyl ester was used instead of the barium salt, the amount of the catalyst was 0.31 g and the reaction temperature was 230° C. to obtain ω-hydroxy pentadecanoic acid. The yield was 30%.

EXAMPLE 14

The same procedure as in Example 12 was repeated except that a barium salt of dodecanedioic acid monomethyl ester (20 mmol) was used instead of the barium salt of pentadecanedioic acid monomethyl ester, and the amount of the catalyst was 0.31 g to obtain ω-hydroxy dodecanoic acid. The yield was 37%.

COMPARATIVE EXAMPLE

The same procedure as in Example 13 was repeated except that disodium salt of decanedioic acid was used as a raw material. However, the reaction was not caused, and only the raw material was recovered.

What is claimed is:

1. A process for producing an ω-hydroxy fatty acid, which comprises subjecting an alkali metal or alkaline earth metal salt of a long-chain dicarboxylic acid monoester having a carbon number of about 9–18 to a reduction with a borohydride compound.

2. The process according to claim 1, wherein said long-chain dicarboxylic acid monoester is a monoester of an aliphatic dicarboxylic acid having a carbon number of 9~18.

3. The process according to claim 1, wherein said alkaline earth metal salt of the long-chain dicarboxylic acid monoester is a barium or calcium salt thereof.

4. The process according to claim 1, wherein said borohydride compound is at least one compound selected from the group consisting of lithium borohydride, calcium borohydride, zinc borohydride, magnesium borohydride, potassium borohydride, beryllium borohydride and barium borohydride.

5. The process according to claim 4, wherein said borohydride compound is at least one compound selected from the group consisting of lithium borohydride, calcium borohydride, magnesium borohydride and zinc borohydride.

* * * * *